United States Patent [19]
Wijay

[11] Patent Number: 5,882,332
[45] Date of Patent: Mar. 16, 1999

[54] DRUG INFUSION CATHETER AND METHOD

[76] Inventor: Bandula Wijay, 1903 Carriage Creek Dr., Friendswood, Tex. 77546

[21] Appl. No.: 870,562
[22] Filed: Jun. 6, 1997
[51] Int. Cl.[6] .................................................. A61M 31/00
[52] U.S. Cl. .............................. 604/53; 604/49; 604/264; 606/159
[58] Field of Search ..................................... 604/264, 280, 604/49, 52, 53, 22, 93; 600/568, 571, 572; 606/159

[56] References Cited

U.S. PATENT DOCUMENTS

| | | | |
|---|---|---|---|
| 5,370,653 | 12/1994 | Cragg | 606/170 |
| 5,419,777 | 5/1995 | Hofling | 604/264 |
| 5,535,756 | 7/1996 | Parasher | 128/756 |
| 5,681,281 | 10/1997 | Vigil et al. | 604/96 |
| 5,693,029 | 12/1997 | Leonhardt | 604/264 |

*Primary Examiner*—John D. Yasko
*Assistant Examiner*—Deborah Blyveis
*Attorney, Agent, or Firm*—Rosenblatt & Redano P.C.

[57] ABSTRACT

A method and apparatus of delivery of a drug (or substance) is disclosed which involves (1) injecting a drug into the tissue of the blood vessel; (2) maintaining the delivery system as symmetrical as possible in tortuous blood vessels, and (3) providing a preferably constant flow of blood during the drug treatment.

29 Claims, 3 Drawing Sheets

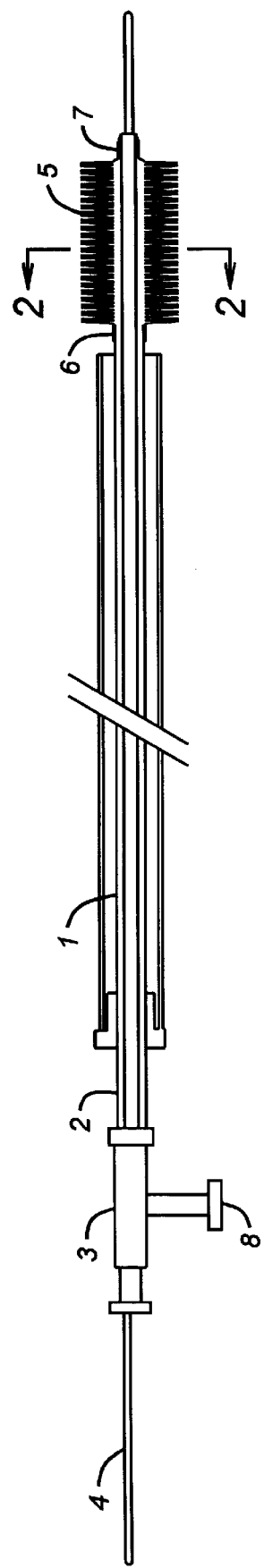
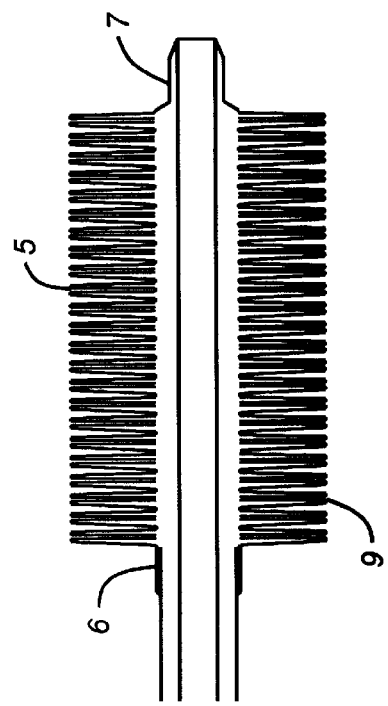

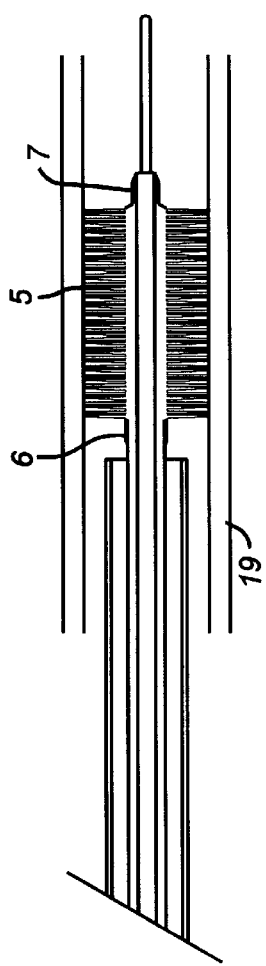
*FIG. 5*
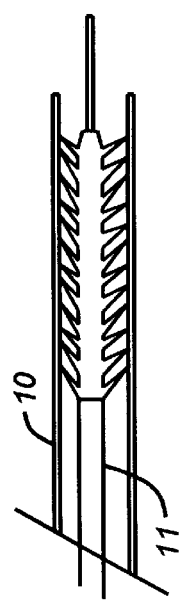
*FIG. 4*
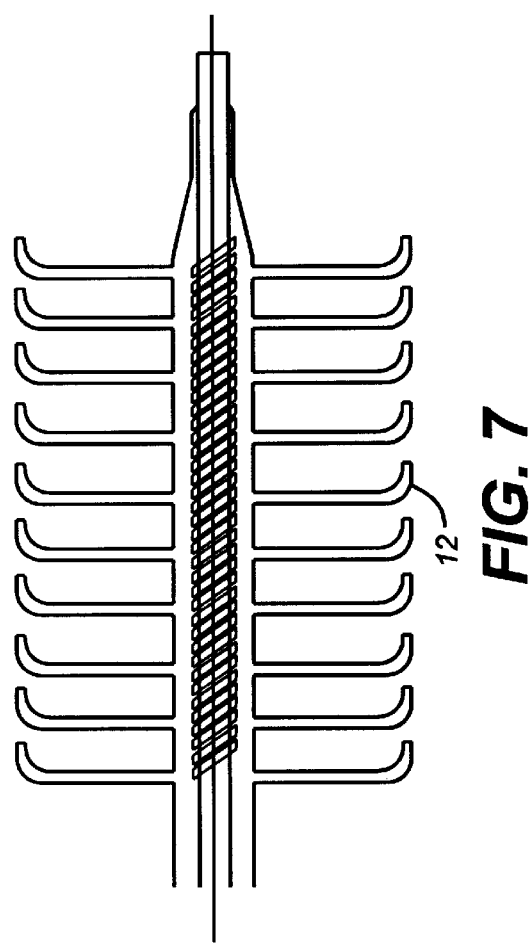
*FIG. 7*
*FIG. 6*

DRUG INFUSION CATHETER AND METHOD

FIELD OF THE INVENTION

The field of this invention relates to blood vessel treatment by drug infusion and other techniques using catheters.

BACKGROUND OF THE INVENTION

For treatment of various diseases in the body, catheters and cannulas are widely used. Using cannulas, a drug can be injected into the tissue whereby the drug is placed in the tissue to be absorbed by diffusion into the tissue cells and subsequently distributed throughout the body using blood as a carrier. Often it is necessary to infuse a drug or substance into the vascular system of the body to treat a specific area of the vascular system. For example, after balloon angioplasty, certain drugs are infused to reduce the risk of re-stenosis of the lesion. These drugs are placed around the lesion to be absorbed by diffusion to the tissue around the lesion. Due to the constant flow of blood in the vessel, the drug infused often gets washed away and only a small amount of the drug is absorbed by the tissue.

In the past, many inventors have tried to solve this problem by providing different solutions. One such method is to use two balloons to occlude the vessel on either side of the lesion (the area of interest) and provide a pool of the drug at the lesion to be absorbed by the tissue by diffusion. This method has the drawback that during balloon inflation, the blood supply is stopped and causes ischemic manifestation to the organ that is supplied by the blood vessel that is to be treated.

Several other devices have also been developed where the drug is infused under pressure to the issue, using balloons.

In another invention, the balloon has small microscopic holes and the balloon is inflated using the drug. The drug is then injected to the tissue through the holes after inflating the balloon.

Others include double-wall balloon where the inner balloon is inflated using an inflation medium while the drug is infused through microscopic holes that are in between in the outer and inner balloon walls.

Various such devices are described in the article by Dr. Steve Bailey in THE JOURNAL OF SEMINARS IN INTERVENTION CARDIOLOGY—LOCAL DRUG DELIVERY, Vol. 1, Issue 1, March 1996, pp. 17–23; by Christine Enger on pp. 27–33; by Mun Hong, pp. 34–35; by Aaron Kaplan, pp. 36–38; by Edoardo Camerzind, pp. 39–40; and by Peter Barath, p. 43.

In most or all of the above cases, a balloon is involved in the delivery of the drug. As a balloon is used as the tool, it invariably causes the occlusion of the artery, which causes ischemic conditions in the organ that is supplied by the blood vessel. This means that the balloon must be deflated quickly after inflation to cause injection of the drug. In all these instances, the drug absorption takes place by diffusion, which is a very slow process.

Another method developed is the needle catheter. The needle catheter is a device having four needles that can be advanced through a tube to protrude outwards to inject the drug into the wall of the blood vessel. These catheters are often bulky and, due to the fact that the needles are metal and stiff, cause damage to the blood vessel wall during the procedure.

SUMMARY OF THE INVENTION

A method and apparatus of delivery of a drug (or substance) is disclosed which involves (1) injecting a drug into the tissue of the blood vessel; (2) maintaining the delivery system as symmetrical as possible in tortuous blood vessels, and (3) providing a preferably constant flow of blood during the drug treatment.

BRIEF DESCRIPTION OF THE DRAWINGS

FIG. 1 is a schematic depiction of the drug infusion apparatus showing a microtubular brush which can be retracted into a sleeve for advancement and retrieval.

FIG. 2 is a sectional view along lines 2—2 of FIG. 1.

FIG. 3 is a detail of the distal end of the apparatus shown in FIG. 1.

FIG. 4 shows the drug infusion catheter retracted into the sheath.

FIG. 5 shows the drug infusion catheter advanced into the blood vessel.

FIG. 6 shows the sheath having a protective cover to protect the patient from radiation.

FIG. 7 shows the drug infusion catheter having a radiation source mounted at the center of the brush apparatus.

DETAILED DESCRIPTION OF THE PREFERRED EMBODIMENT

Figure 9:
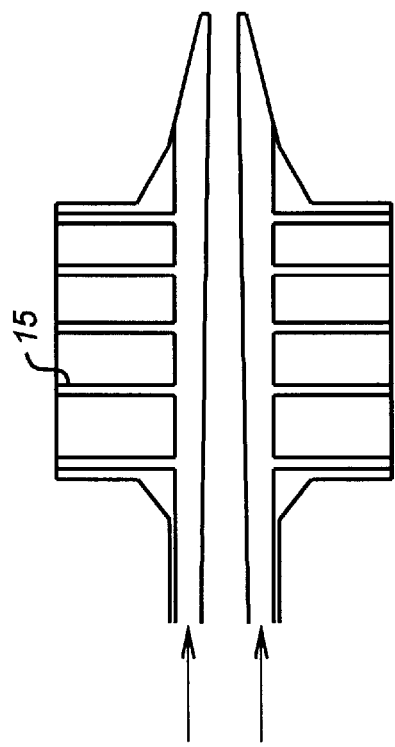
FIG. 9 shows an alternate design using rib structure instead of bristles.
Figure 8:
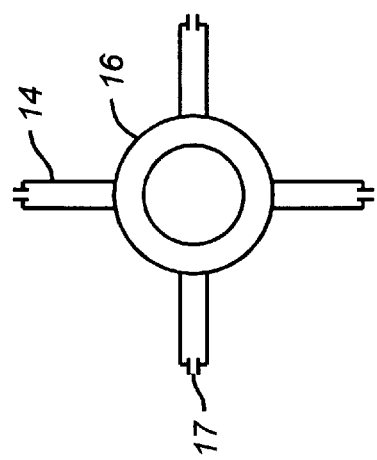
FIG. 8 shows a cross-section of alternate design instead of bristles.

The objective of this invention to provide a method of delivery of the drug (or substance) by (1) injecting it into the tissue of the blood vessel; (2) to maintain the system as symmetrical as possible in tortuous blood vessels, and (3) to provide the constant flow of blood during the drug treatment.

This is achieved by a device similar to the one in FIG. 1. The device (catheter) is made from two coaxial tubes, 1 and 2. In the proximal end, the tubes are connected to a plastic adapter 3. The catheter can be advanced to the vascular system over a guidewire 4. At the very distal end, the coaxial tube is fitted with a molded plastic brush-like apparatus 5. The plastic brush-like apparatus has bristles that are hollow. The proximal end of the brush apparatus is attached to the end 6 of the coaxial tube 2, and the distal end of the brush apparatus 5 is attached to the coaxial tube 1 at end 7. A drug or substance can be injected from a side port 8 in the proximal adapter 3. Injection can be high pressure up to 600–700 psi. Depending on the size of the passage in the bristle and the backpressure applied, the drug will be injected at a high velocity, and at a velocity high enough, the drug will be injected to the tissue wall. Once the drug is injected to the tissue wall, it will be transported by diffusion.

The bristle apparatus 5 can be made in different diameters, such as 2.0 mm, 2.5 mm, 4.0 mm, so as to fit the blood vessel under treatment. The bristle apparatus can be provided with 4, 8, or 12 bristles in a given row, as shown in FIG. 2. Along the length of the bristle apparatus, 10–20 rows of bristles can also be provided. The number of rows and number of hollow bristles in a row are for example only. Each row is in a particular transverse plane; however, a spiral distribution pattern or a random pattern of individual bristles can also be used. The bristles are preferably made from soft plastics so that when the catheter is advanced out of sheath 10, as shown by comparing FIGS. 4 and 5, the tips of the bristles do not damage the artery wall. For this purpose, nylon, polyethylene, high-density polyethylene (HDPE), polyurethane, silicone, polyvinyl chloride (PVC), or acrylonitrile butadiene styrene (ABS) are suitable polymer materials. The bristle structure can be a flexible tube that is bent under a sheath or a multi-component tube with telescoping segments that extends radially upon fluid pressure applied thereto.

Inasmuch as there is no balloon involved in this design, blood would continue to flow without hindrance distal to the area treated and would not cause any problems of ischemia, which is caused when the flow of blood is restricted by the use of a balloon device. Since the bristles are soft, they will not cause mechanical damage to the blood vessel wall as is the case with balloons having needle structures or catheters with rigid metallic needles.

The bristles 5 in the present invention are tapered to a point, providing flexibility as well as a point that will help to "fix" the tip of the needle to the inner surface of the blood vessel during drug infusion.

FIG. 4 shows a sheath 10 in which the catheter assembly 11 is kept while it is advanced into the vascular system to prevent any damage. The catheter assembly 11 can be advanced over the guidewire 4 into the lesion location for injection of the drugs. After injection of the drugs, the catheter 11 can be retracted into the sheath 10 by moving the sheath 10 forward while holding the catheter 11, and the entire assembly 11 can be withdrawn from the vascular system without damage to the inner lining of the blood vessel.

In an alternate design, instead of separate and discrete bristles, rows of ribs 14, 4–10 in number, can be provided extending radially in general alignment such as along the length of the catheter as shown in FIG. 9 or a spiral pattern. The ribs 14 are spaced apart to allow blood or other fluid to flow through the vessel without significant restriction as drugs are delivered to the vessel wall through insert tubes 17. These ribs have small diameter channels 15 molded in so that the drug can be infused from the annular space between the two tubes to the blood vessel wall. Just as in the previous disclosure, these ribs are made of very soft plastic or rubber material to prevent trauma to the inner lining of the blood vessel. They are retained in a flexed position by a removable retaining sleeve. When the sleeve is retracted, the resiliency of the ribs aids in their expansion. Alternatively, the ribs 14 can be sufficiently flexible so that they don't need to be retained but they expand radially as passages 15 are pressurized. The concentric wall of the structure is made thin enough so that when the catheter is pressurized, the tube assembly would expand about 1–5 mm, enabling the ribs or bristles to touch the inner wall of the blood vessel. Without the pressure the ribs/bristles are somewhat restricted. At the end of the bristles/ribs, sharp metal tube(s) 17 can be molded in place to enhance the puncturing of the blood vessel in order to deliver the drug more effectively. The present design also allows blood to flow without hindrance during the drug infusion, thus maintaining proper functions of the organ diffused.

Another use for the present invention is to treat the lesion with radiation. In most instances, gamma or beta radiation is used to treat lesions to reduce the growth of cells (neointima) after balloon angioplasty. An apparatus, as in FIGS. 6 and 7, describes a means of providing radiation to a lesion. In this instance, the bristles 12 can be either hollow or solid. They are preferably bent at the end to produce a smooth surface and a footing. The radiation material is wound or placed on the inner tube. Preferably, a coil spring of thickness 0.004–0.006" can be used. The material of construction of the radiation material can be any material that absorbs radiation and emits radiation. A certain degree of radiopathy is preferred so that the radiation source is visible under fluoroscopy. When the radiation source is made into a flexible spring, the trackability of the catheter through the vascular system is enhanced. In this case also, the catheter is advanced to the lesion in the vascular system in a sheath. After placing the sheath proximal to the lesion, the catheter is advanced to expose the lesion to radiation. Once the radiation is completed, the catheter is pulled back into the sheath under the protective cover 13. The protective cover stops any radiation from affecting other parts of the body or the health professionals using radiation systems.

The foregoing disclosure and description of the invention are illustrative and explanatory thereof, and various changes in the size, shape and materials, as well as in the details of the illustrated construction, may be made without departing from the spirit of the invention.

I claim:

1. A fluid infusion catheter for use in a blood vessel defined by a wall, comprising:

an elongated tubular body having a proximal and a distal end and an outer surface and defining a passage therein;

at least one flexible bristle fixedly mounted adjacent said outer surface of said body; said bristle having a proximal and a distal end and a passage therethrough in flow communication with said passage in said body so that a fluid can be directed through said body and said bristle and to the vessel wall without occlusion of the vessel.

2. The catheter of claim 1, wherein:

said body further comprises a sheath to retain said bristle in a retracted position, said sheath being retractable from over said bristle to allow it to extend toward the vessel wall.

3. The catheter of claim 2, wherein:

said bristle, when extended, and said body further comprise longitudinal axes which intersect.

4. The catheter of claim 3, wherein:

said bristle further comprises a plurality of radiating bristles in a single plane which defines a row of said bristles.

5. The catheter of claim 4, wherein:

said row further comprises a plurality of rows of said bristles.

6. The catheter of claim 5, further comprising:

a bend on said distal end of a plurality of said bristles such that upon retraction of said sheath, said distal end of said bristles is in substantial alignment with the vessel wall.

7. The catheter of claim 6, wherein:

said body further comprises a radiation material;

said sheath comprises a shield for said radiation material.

8. The catheter of claim 5, wherein:

said bristles are of a predetermined length such that upon retraction of said sheath, said distal end of said bristles flexes to a position in close proximity to the vessel wall.

9. The catheter of claim 8, wherein:

said bristles upon flexing are in contact with the vessel wall.

10. The catheter of claim 9, wherein:

said bristles are externally tapered down from said proximal end of said bristles adjacent said body to said distal end of said bristles.

11. The catheter of claim 10, wherein:

said radiating bristles act to centralize said body in the vessel.

12. The catheter of claim 11, wherein:

said body comprises an outer tube surrounding an inner tube defining an annulus therebetween which serves as said passage;

said passage in said bristles is in flow communication with said annulus for delivery of fluid under pressure to the vessel wall.

13. The catheter of claim 12, wherein:

said inner tube has a passage therethrough which can accept a guidewire for advancement of the catheter.

14. The catheter of claim 2, wherein:

said bristle is of a predetermined length such that upon retraction of said sheath, said distal end of said bristle flexes to a position in close proximity to the vessel wall.

15. The catheter of claim 14, wherein:

said bristle upon flexing is in contact with the vessel wall.

16. The catheter of claim 2, wherein:

said bristle is externally tapered down from said proximal end of said bristle adjacent said body to said distal end of said bristle.

17. The catheter of claim 4, wherein:

said radiating bristles act to centralize said body in the vessel.

18. The catheter of claim 1, wherein:

said body comprises an outer tube surrounding an inner tube defining an annulus therebetween which serves as said passage;

said passage in said bristle is in flow communication with said annulus for delivery of fluid under pressure to the vessel wall.

19. The catheter of claim 18, wherein:

said inner tube has a passage therethrough which can accept a guidewire for advancement of the catheter.

20. A method of treating a vessel defined by a wall with a fluid without occlusion thereof, comprising:

mounting at least one flexible bristle adjacent the outer surface of an elongated body of a catheter;

inserting into a vessel said catheter having said elongated body with a passage in flow communication with said bristle with a passage therethrough;

retaining said bristle in a flexed state adjacent said outer surface of said elongated body during said inserting;

allowing said bristle to flex toward the vessel wall at a predetermined location;

pumping fluid through said passages in said body and bristle and against the vessel wall while blood flows around said body and bristle.

21. The method of claim 20, further comprising:

retaining said bristle with a movable sheath.

22. The method of claim 21, further comprising:

using a plurality of rows of bristles extending from said body;

allowing said bristles to flex to close proximity with the vessel wall upon retraction of said sheath.

23. A method of treating a vessel with a radiation source, comprising:

providing a source on a catheter body having an outer surface;

providing a plurality of bristles having a proximal and a distal end, said bristles being fixedly mounted adjacent said outer surface of said body;

providing a movable sheath over said body which shields said source and holds said bristles in a retracted position;

advancing said body with said source while said source is covered by said sheath to a predetermined location in a vessel;

exposing said bristles and said source by retraction of said sheath;

allowing said bristles to extend toward the vessel wall;

centralizing said source in the vessel with said bristles.

24. The method of claim 23, further comprising:

providing a bend on said distal end of a plurality of said bristles;

placing said distal end in substantial alignment with the vessel wall as a result of retraction of said sheath.

25. The method of claim 24, further comprising:

providing a passage through said body and said bristles to allow fluid to be pumped therethrough.

26. The method of claim 24, further comprising:

allowing blood to flow around said bristles when in contact with the vessel.

27. A fluid infusion catheter for use in a blood vessel defined by a wall, comprising:

an elongated tubular body having a proximal and a distal end and an outer surface and defining a passage therein;

at least one flexible bristle having a passage therethrough in flow communication with said passage in said body so that a fluid can be directed through said body and said bristle and to the vessel wall without occlusion of the vessel;

said bristle is selectively retained adjacent said outer surface of said body.

28. A method of treating a vessel defined by a wall with a fluid without occlusion thereof, comprising:

inserting into a vessel a catheter having an elongated body with a passage in flow communication with at least one flexible bristle with a passage therethrough;

retaining said bristle in a retracted state with a movable sheath during said inserting;

allowing said bristle to flex toward the vessel wall at a predetermined location;

pumping a fluid through said passages in said body and bristle and against the vessel wall while blood flows around said body and bristle;

using a plurality of bristles which, upon retraction of said sheath from said body, flex to extend radially in contact with said wall to centralize said body in the vessel.

29. A method of treating a vessel defined by a wall with a fluid without occlusion thereof, comprising:

inserting into a vessel a catheter having an elongated body;

using concentric tubes to create an annular passage in said body with said annular passage in flow communication with a plurality of bristles with a passage therethrough;

advancing said concentric tubes over a guidewire;

using said bristles to close off an end of said annular passage;

providing a taper on said bristles;

using a plurality of rows of bristles extending from said body;

retaining said bristles in a retracted state with a movable sheath during said inserting;

allowing said bristles to flex toward the vessel wall at a predetermined location upon retraction of said sheath;

allowing said bristles to contact the vessel upon retraction of said sheath, pumping fluid through said annular passage in said body and said bristles and against the vessel wall while blood flows around said body and bristles.

* * * * *